United States Patent [19]

Brown et al.

[11] Patent Number: 4,521,625

[45] Date of Patent: Jun. 4, 1985

[54] DIOXOCYCLOBUTENE COMPOUNDS

[75] Inventors: Thomas H. Brown, Tewin; Rodney C. Young, Bengeo, both of England

[73] Assignee: Smith Kline & French Laboratories Limited, Welwyn Garden City, England

[21] Appl. No.: 535,468

[22] Filed: Sep. 26, 1983

[30] Foreign Application Priority Data

Oct. 2, 1982 [GB] United Kingdom ................ 8228207
Nov. 13, 1982 [GB] United Kingdom ................ 8232468

[51] Int. Cl.$^3$ .............................................. C07C 87/45
[52] U.S. Cl. .................................................... 564/461
[58] Field of Search ....................................... 564/461

[56] References Cited

U.S. PATENT DOCUMENTS

| 3,017,395 | 1/1962 | Elam et al. | 54/461 X |
| 3,232,973 | 1/1966 | Bayer et al. | 564/461 X |
| 3,287,390 | 11/1966 | Poos et al. | 564/461 X |
| 4,062,863 | 12/1977 | Ganellin et al. | 564/461 X |
| 4,390,701 | 6/1983 | Algieri et al. | 564/461 X |
| 4,395,553 | 7/1983 | Algieri et al. | 564/461 X |

FOREIGN PATENT DOCUMENTS

| 1531943 | 6/1968 | France | 564/461 |
| 2505835 | 11/1982 | France | 564/461 |

OTHER PUBLICATIONS

Morrison et al., "Organic Chemistry", 3rd Ed., Allyn & Bacon, Inc., Boston (1973), pp. 556 & 557.
Schmidt, "Synthesis", p. 961–994, 12/1980.
*Derwent Abstract* 02282J (Abstract of Belgian 893,236 Published Nov. 18, 1982).

*Primary Examiner*—Paul F. Shaver
*Attorney, Agent, or Firm*—Joan S. Keps; Richard D. Foggio; Alan D. Lourie

[57] ABSTRACT 1-(Hydroxypropylamino)-2-aminocyclobut-1-ene-3,4-dione compounds are disclosed as useful intermediates in the preparation of histamine $H_2$-antagonists.

4 Claims, No Drawings

DIOXOCYCLOBUTENE COMPOUNDS

This inventin relates to dioxocyclobutene derivatives and their use in the preparation of histamine antagonists.

Histamine, a physiologically active compound endogenous in mammals, exerts its action by interacting with certain sites called receptors. One type of receptor is known as a histamine $H_1$-receptor (Ash and Schild, Brit. J. Pharmac. Chemother. 27 427 (1966)) and the actions of histamine mediated through these receptors are blocked by drugs commonly called "antihistamines" (histamine $H_1$-antagonists) a common example of which is mepyramine. A second type of histamine receptor is known as the $H_2$-receptor (Black et al. Nature 1972, 236, 385). These receptors are not blocked by mepyramine but are blocked by burimamide. Compounds which block these histamine $H_2$-receptors are called histamine $H_2$-antagonists.

Histamine $H_2$-antagonists are useful in treating disease conditions caused by the biological effects of histamine mediated through $H_2$-receptors, for example, as inhibitors of gastric acid secretion, in the treatment of inflammation mediated throught histamine $H_2$-receptors and as agents which act on the cardiovascular system, for example, as inhibitors of effects of histamine on blood pressure mediated through histamine $H_2$-receptors.

Cimetidine is an example of a histamine $H_2$-antagonist. Cimetidine has been shown to be useful in the treatment of duodenal, gastric, recurrent and stomal ulceration, and reflux eosophagitis and in the management of patients who are at high risk from haemorrhage of the upper gastrointestnal tract.

In some physiological conditions the biological actions of histamine are mediated through both histamine $H_1$- and $H_2$-receptors and blockade of both types of receptors is useful. These conditions include inflammation mediated by histamine, for example skin inflammation, and those hypersensitivity responses due to the action of histamine at $H_1$- and $H_2$-receptors, for example allergies.

We have discovered novel intermediates that are useful in the preparation of certain histamine antagonists.

Accordingly the present invention provides a compound of the formula (I)

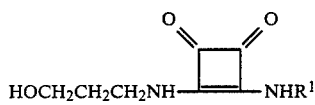

wherein $R^1$ is hydrogen or $C_{1-6}$alkyl group.

Suitably $R^1$ is hydrogen, methyl, ethyl or propyl. Preferably $R^1$ is hydrogen as such compounds lead to histamine $H_2$-antagonists with good activity.

The compounds of the formula (I) are prepared by a process which comprises reacting a compound of the formula (II) with 3-amino-propanol or a chemical equivalent thereof.

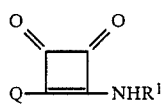

wherein $R^1$ is as hereinbefore defined and Q is a group displaceable by amine.

Suitably Q is $C_{1-6}$alkoxy, halo or a $C_{1-6}$alkylthio moiety, for example methylthio, methoxy or ethoxy. Of these methoxy is preferred. The reaction may be performed in the absence of solvent or in a solvent for example methnonal, ethanol or acetonitrile. In the presence of a solvent the reaction temperature may be for example from ambient to reflux. In the absence of a solvent the reaction temperature is conveniently at an elevated temperature, for example about 120°–160° C.

The compounds of the formula (II) are preparable by the methods of U.S. Pat. No. 4,062,863.

The compounds of the formula (I) may be used with compounds of the formula (III):

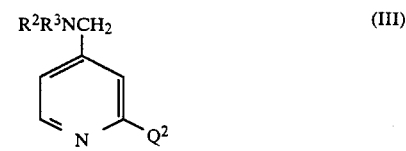

to prepare compounds of the formula (IV):

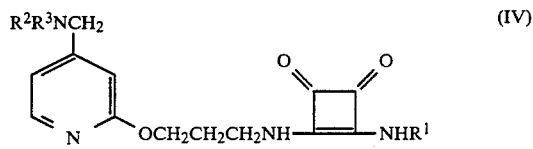

wherein $R^1$ is as hereinbefore defined, $Q^2$ is a group displaceable by hydroxy (suitably chloro or bromo) and $R^2$ and $R^3$ are independently hydrogen or $C_{1-6}$alkyl or $R^2R^3N$ represents 2,2,2-trifluoroethylamino; or $R^2$ or $R^3$ form a —$(CH_2)_n$— linkage wherein n is 4-6, so that together with the nitrogen atom to which they are attached they form a 5-7 membered ring. The reaction of a compound of the formula (III) with a compound of the formula (I) is generally performed under basic conditions, for example the anion of the compound of the formula (I) may be generated, for example using excess sodium hydride in a suitable solvent.

The compounds of the formula (I) may be converted to compounds of the forumula (V):

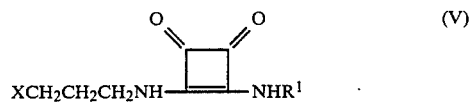

wherein $R^1$ is as hereinbefore defined and X is a group displaceable by hydroxy or the equivalent thereof.

Suitably X is bromo or chloro.

The reaction is conveniently performed at a non-extreme temperature such as between 0° C. and reflux, conveniently ambient, in the presence of a substantially inert solvent for example dichloromethane or chloroform. Suitable agents for the introduction of the group X are halogenating agents, for example thionyl chloride or thionyl bromide in the presence of a base such as pyridine or triethylamine.

The compounds of the formula (V) are novel and as such form part of this invention.

In a further aspect the present invention provides a process for the preparation of a compound of the formula (VI):

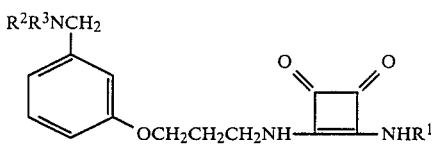

wherein R[1] R[2] and R[3] are as hereinbefore defined, which process comprises reacting a compound of the formula (V) as hereinbefore defined with a compound of the formula (VII) or derivative thereof that permits reaction to occur:

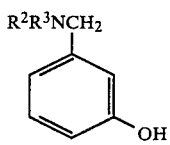

wherein R[2] and R[3] are as hereinbefore defined.

The compounds of the formula (VII) are preparable by the methods of Turner and Gearien, J. Org. Chem. 24, p 1952 (1959).

Suitably the reaction is performed under basic conditions, for example the anion of the compound of the formula (VII) may be generated, for example using sodium hydride. The reaction is performed in a suitable aprotic solvent for example dimethylformamide at a non-extreme temperature for example between 0° C. and 100° C., suitably between ambient and 70° C.

Preferably in the reaction of compounds of the formulae (V) and (VII), X is chloro or bromo. Preferably R[2] and R[3] are both methyl or are joined so as to form together with the nitrogen atom a piperidino group. We have found the compound of the formula (VI) wherein R[3]R[3]N is piperidino and R[1] is hydrogen to be of particular interest as an H$_2$-antagonist. This compound may also be prepared by reacting a compound of the formula (VIII):

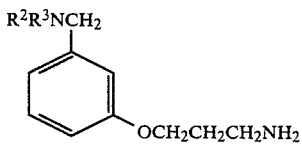

wherein R[2] and R[3] are as hereinbefore defined with a compound of the formula (II) as hereinbefore defined, under conditions analogous to those described for the reaction of the compounds of the formula (I) and 3-aminopropanol.

The following Examples serve to illustrate this invention.

EXAMPLE 1

1-amino-2-(3-hydroxypropylamino)cyclobut-1-ene-3,4-dione

1-Amino-2-methoxycyclobut-1-ene-3,4-dione (1.27 g) and 3-hydroxypropylamine (0.75 ) were refluxed in ethanol (25 ml) for 4 hours. The reaction mixture was cooled and the solid product collected by filtration. This was washed with ethanol and dried to afford the title compound (1.3 g), m.p. 256°–258° C.; found C 49.27, H 5.88, N 16.38 (calculated C 49.41, H 5.92, N 16.46); δppm 1.69 (2H,m), 3.4–3.7 (4H, m), 4.47 (1H, t, OH), 7.32 (3H, broad, amino protons).

EXAMPLE 2

1-Amino-2-(3-chloropropylamino)cyclobut-1-ene-3,4-dione

A mixture of 1-amino-2-(3-hydroxypropylamino)cyclobut-1-ene-3,4-dione (1.0 g) and pyridine (0.5 ml) in chloroform (100 ml) was cooled to 0° C. To this was added dropwise thionyl chloride (4.38 g) in chloroform (30 ml) and the reaction mixture was stirred overnight at room temperature. There was solid remaining so more thionyl chloride (4.38 g) was added, the solid slowly dissolving, and the reaction mixture was left to stand for 60 hours. The mixture was evaporated under reduced pressure to afford an oily residue, which on the addition of water gave a solid which was collected by filtration and dried to give the title compound (0.73 g); δppm 2.0 (2H, m), 3.5–3.8 (4H, m), 7.45 (broad m); m/e 190, 188, 152, 134, 132, 97, 96, 69.

EXAMPLE 3

1-[3-[3-(Piperidinomethyl)phenoxy]prop-1-ylamino]-2-amino-cyclobut-1-ene-3,4-dione A mixture of sodium hydride (0.16 g; 50% dispersion in oil) in dimethylformamide (20 ml) was cooled to 0° C. To this was added dropwise 3-(piperidinomethyl)-phenol (0.6 g) in dimethylformamide (10 ml) and the mixture was allowed to warm to room temperature and stirred for 150 minutes. 1-Amino-2-(3-chloropropylamino)cyclobut-1-ene-3,4-dione (0.6 g) in dimethylformamide (30 ml) was added dropwise and the reaction mixture stirred for 20 hours. On examination by thin layer chromatography it was found that the reaction had not gone to completion. Sodium hydride (0.16 g; 50% dispersion in oil) was added, the reaction mixture stirred for 3 hours at room temperature, then stirred for 3 hours at 65° C. and cooled. The reaction mixture was evaporated under reduced pressure, the residue was treated with dilute sodium hydroxide and extracted into chloroform/methanol (9:1). The chloroform/methanol extracts were combined, dried oer magnesium sulphate, filtered and evaporated under reduced pressure to give the title compound; δppm 1.45 (6H, m), 2.00 (2H, m), 2.40 (4H, m), 3.43 (2H, s), 3.65 (2H, m), 4.03 (2H, t), 6.85 (3H, m), 7.23 (1H, t), 7.50 (broad m) (spectrum consistent with an authentic sample).

What is claimed is:

1. A compound of the formula (I):

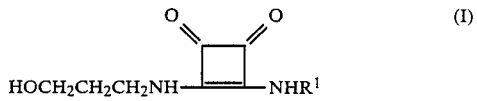

wherein R[1] is hydrogen or a C$_{1-6}$alkyl group.

2. A compound according to claim 1 wherein R[1] is hydrogen.

3. A compound of the formula (V):

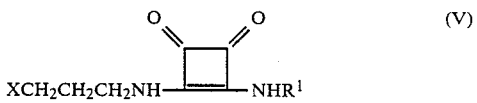

wherein R[1] is hydrogen or a C$_{1-6}$alkyl group and X is a group displaceable by hydroxy or the equivalent thereof.

4. A compound according to claim 3 wherein X is bromo or chloro.

* * * * *